United States Patent [19]

Smithers

[11] Patent Number: 4,806,563

[45] Date of Patent: Feb. 21, 1989

[54] N-[4-O-HYDROXYPHENYL-1,3-DIOXAN-5-YLHEXENOYL]SULPHONAMIDES

[75] Inventor: Michael J. Smithers, Macclesfield, United Kingdom

[73] Assignee: Imperial Chemical Industries PLC, London, England

[21] Appl. No.: 928,454

[22] Filed: Nov. 10, 1986

[30] Foreign Application Priority Data

Nov. 12, 1985 [GB] United Kingdom ................. 8527862
May 8, 1986 [GB] United Kingdom ................. 8611174

[51] Int. Cl.[4] .................. A61K 31/335; C07D 319/06
[52] U.S. Cl. ..................................... 514/452; 549/373
[58] Field of Search ......................... 549/373; 514/452

[56] References Cited

U.S. PATENT DOCUMENTS 4,567,197 1/1986 Brewster et al. ................. 514/452

*Primary Examiner*—Nicky Chan
*Attorney, Agent, or Firm*—Cushman, Darby & Cushman

[57] ABSTRACT

The invention concerns novel N-[4(Z)-6-(4-o-hydroxyphenyl-1,3-dioxan-cis-5-yl)hexanoyl]sulphonamide derivatives of formula I of value as therapeutic agents. $R^1$ is typically an alkoxyalkyl or phenoxyalkyl radical as defined hereinafter and $R^2$ is alkyl, benzyl or phenyl. The invention also discloses salts of the formula I compounds as well as pharmaceutical compositions containing the compounds and processes for the production of the compounds.

11 Claims, No Drawings

N-[4-O-HYDROXYPHENYL-1,3-DIOXAN-5-YLHEXENOYL]SULPHONAMIDES

This invention concerns novel amide derivatives and, more particularly novel N-[4(Z)-6-(4-o-hydroxyphenyl-1,3-dioxan-cis-5-yl)hexenoyl]sulphonamide derivatives which antagonise one or more of the actions of thromboxane $A_2$ (hereafter referred to as "$TXA_2$") and which are of value as therapeutic agents. The invention also concerns novel pharmaceutical compositions containing one of the novel derivatives and processes and intermediates for use in the manufacture of the novel amide derivatives.

It is known that $TXA_2$ is a potent aggregator of blood platelets and a powerful vasoconstrictor. $TXA_2$ is also a potent constrictor of bronchial and tracheal smooth muscle. $TXA_2$ may therefore be involved in a wide variety of disease conditions, for example ischaemic heart disease such as myocardial infarction, angina, cerebrovascular disease such as transient cerebral ischaemia, migraine and stroke, peripheral vascular disease such as atherosclerosis, microangiopathy, hypertension and blood clotting defects due to lipid imbalance, and pulmonary disease such as pulmonary embolism, bronchial asthma, bronchitis, pneumonia, dyspnoea and emphysema. Accordingly, compounds which antagonise the actions of $TXA_2$ may be expected to have therapeutic value in the prevention or treatment of any one or more of the above mentioned diseases or any other disease conditions in which it is desirable to antagonise the actions of $TXA_2$.

In our European patent application, publication number 94239, there is described a series of 4-phenyl-1,3-dioxan-5-ylalkenoic acid derivatives of the formula Z having cis relative stereochemistry at positions 4 and 5 of the dioxane ring and wherein Ra and Rb are variously hydrogen, alkyl, halogenoalkyl, alkenyl and optionally substituted aryl or arylalkyl, Rc is hydroxy, alkoxy or alkanesulphonamido, n is 1 or 2, A is ethylene or vinylene, Y is (2-5C)polymethylene optionally substituted by alkyl and benzene ring B bears one or two optional substituents. We have now discovered (and herein lies the basis of our invention). that particularly useful $TXA_2$ antagonism is also shown by a novel group of amide derivatives of formula Z in which benzene ring B is o-hydroxyphenyl, n is 1, A is cis-vinylene, Y is ethylene and Rc is sulphonamido, as defined below.

According to the invention there is provided a N-[4(Z)-6-(4-o-hydroxyphenyl-1,3-dioxan-5-yl)hexenoyl]-sulphonamide of the formula I set out hereinafter wherein $R^1$ is a group of the formula $R^3O.CR^4R^5-$ in which $R^3$ is (1–6C)alkyl or phenyl, the latter optionally bearing a substituent selected from halogeno, cyano, nitro, trifluoromethyl and (1–4C)alkoxy, and $R^4$ and $R^5$ are independently (1–4C)alkyl; and $R^2$ is (1–6C)alkyl, benzyl or phenyl, the latter two of which may optionally bear a halogeno, (1–4C)alkyl, (1–4C)alkoxy, trifluoromethyl, cyano or nitro substituent; and the substituents at positions 4 and 5 of the dioxane ring in formula I and the substituent $R^1$ have cis-relative stereochemistry; or a pharmaceutically acceptable salt therof.

It will be appreciated that the compounds of formula I possess asymmetric carbon atoms and may exist and be isolated in racemic and optically active forms. The invention includes both the racemic forms and any optically active form (or mixtures thereof) which is capable of antagonising one or more of the actions of $TXA_2$, it being well known in the art how to prepare individual optical isomers (for example by synthesis from optically active starting materials or resolution of a racemic form) and how to determine the $TXA_2$ antagonist properties using one or more of the standard tests referred to hereafter.

In the chemical formulae attached hereto, although a particular configuration is shown, this does not necessarily correspond to the absolute configuration.

A particular value for $R^4$ or $R^5$ is, for example, methyl or ethyl, and preferably methyl. It is generally preferred that $R^4$ and $R^5$ total together no more than 4 carbon atoms.

A particular value for an optional substituent which may be present on $R^2$ or $R^3$ when it is phenyl or on $R^2$ when it is benzyl, as defined above, is, for example: fluoro, chloro or bromo, for halogeno; methyl or ethyl, for (1–4C)alkyl; and methoxy or ethoxy, for (1–4C)alkoxy.

Particular pharmaceutically acceptable salts of the sulphonamide derivatives of formula I are, for example: alkali metal and alkaline earth metal salts, such as lithium, sodium, potassium, magnesium and calcium salts; aluminium and ammonium salts; and salts with organic amines and quaternary bases forming physiologically acceptable cations, such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

Specific values for $R^1$ which are of special interest include for example, 1-[(1–4C)alkoxy]-1-methylethyl, and 1-methyl-1-phenoxyethyl (optionally bearing a fluoro, chloro, bromo, cyano or nitro substituent on the phenoxy moiety) and for $R^2$ include, for example, methyl, ethyl and phenyl optionally bearing a fluoro, chloro, bromo, cyano, nitro, trifluoromethyl or methoxy substituent.

A specific value for $R^2$ when it is (1–6C)alkyl is for example, methyl, ethyl, propyl or isopropyl.

A preferred value for $R^1$ is 1-methoxy-1-methylethyl or 1-methyl-1-phenoxyethyl, and for $R^2$ is methyl or ethyl.

A particular value for $R^3$ when it is (1–6C)alkyl is, for example, methyl, ethyl or propyl.

A specific compound of formula I of particular interest is set out in the accompanying Example 1. This compound, or a pharmaceutically acceptable salt thereof is provided as a separate feature of the invention.

The compounds of formula I may be manufactured by conventional procedures of organic chemistry well known in the art for the manufacture of structurally analogous compounds. Such procedures are provided as a further aspect of the invention and are illustrated by the following processes in which $R^1$, $R^2$, $R^3$, $R^4$ and $R^5$, have any of the meanings herein above:

(a) An aldehyde of the formula II is reacted with a Wittig reagent of the formula $R'_3P=CH.(CH_2)_2.CO.N^-.SO_2R^2$ $M^+$ wherein R' is (1–6C)alkyl or aryl (especially phenyl) and $M^+$ is a cation, for example an alkali metal cation, such as the lithium, sodium or potassium cation. The process in general produces compounds of formula I in which the substituents adjacent to the double bond have predominantly cis-relative stereochemistry i.e. the 'Z' isomer.

The process is conveniently performed in a suitable solvent or diluent, for example an aromatic solvent such as benzene, toluene or chlorobenzene, an ether such as 1,2-dimethoxyethane, t-butyl methyl ether, dibutyl ether or tetrahydrofuran, in dimethyl sulphoxide or tetramethylene sulphone, or in a mixture of one or more such solvents or diluents. The process is generally performed at a temperature in the range, for example, $-80°$ C. to 40° C., but is conveniently performed at or near room temperature, that is in the range 0° to 35° C.

(b) A phenol derivative of the formula III, wherein R″ is a suitable protecting group, for example (1–6C)alkyl (such as methyl or ethyl), acyl (such as acetyl, benzoyl, methanesulphonyl or p-toluenesulphonyl), allyl, tetrahydropyran-2-yl or trimethylsilyl, is deprotected.

The precise deprotection conditions used depend on the nature of the protecting group R″. Thus, for example, when it is methyl or ethyl the deprotection may be carried out by heating with sodium thioethoxide in a suitable solvent (such as N,N-dimethylformamide or 1,3-dimethyl-3,4,5,6-tetrahydro-2(1H)-pyrimidinone) at a temperature in the range, for example, 60°–160° C. When the protecting group is acyl it may be removed, for example, by hydrolysis in the presence of a base (such as sodium or potassium hydroxide) in a suitable aqueous solvent [such as an aqueous (1–4C)alkanol] at a temperature in the range, for example, 0°–60° C. When the protecting group is allyl or tetrahydropyran-2-yl it may be removed, for example, by treatment with strong acid such as trifluoroacetic acid and when it is trimethylsilyl, it may be removed, for example, by reaction with aqueous tetrabutylammonium fluoride or sodium fluoride, using a conventional procedure.

(c) An erythro-diol derivative of the formula IV, wherein one of $Q^1$ and $Q^2$ is hydrogen and the other is hydrogen or a group of the formula —$CRaRb.OH$ (wherein Ra and Rb are the same or different (1–4C)alkyl), is reacted with an aldehyde of the formula $R^1.CO.H$, or with an acetal hemiacetal or hydrate thereof.

The aldehyde [or its hydrate, or its acetal or hemiacetal with a (1–4C)alkanol (such as methanol or ethanol)] is generally used in excess.

The reaction is generally performed in the presence of an acid catalyst, such as hydrogen chloride, hydrogen bromide, sulphuric acid, phosphoric acid, methanesulphonic acid, p-toluenesulphonic acid, or an acidic resin, conveniently in the presence of a suitable solvent or diluent, such as toluene, xylene or an ether, for example tetrahydrofuran, dibutyl ether, methyl t-butyl ether or 1,2-dimethoxyethane, and at temperature in the range, for example 0° to 80° C.

Those starting materials of formula IV wherein $Q^1$ and $Q^2$ are both hydrogen may be obtained, for example, by mild acid catalysed hydrolysis or alcoholysis of the dioxane ring of a compound of formula V wherein Ra and Rb are both alkyl, such as methyl or ethyl. The hydrolysis or alcoholysis will normally be carried out a temperature in the range 10° to 80° C. using an aqueous mineral acid such as hydrochloric acid, in an alkanol (such as ethanol or 2-propanol) or an ether (such as tetrahydrofuran), as solvent.

Those starting materials of formula IV wherein one of $Q^1$ and $Q^2$ is hydrogen and the other is a group of the formula —$CRaRb.OH$ are intermediates in the above-mentioned formation of the starting materials of formula IV wherein $Q^1$ and $Q^2$ are both hydrogen. However, said intermediates are not normally isolated or characterised. Accordingly, the invention also provides a modification of process (c) which comprises reacting a compound of formula V wherein one of Ra and Rb is hydrogen, methyl or ethyl and the other is methyl or ethyl, with an excess of an aldehyde of the formula $R^1.CO.H$ or an acetal, hemiacetal or hydrate thereof, in the presence of an acid-catalyst(such as one of those given above), conveniently at a temperature in the range, for example, 10° to 80° C. and optionally in the presence of a suitable solvent or diluent (such as one of those given above).

The starting materials for use in the above processes may be made by general procedures of organic chemistry, known for the preparation of structurally related compounds, for example by analogy with those procedures disclosed in European patent application, publication No. 94239.

The protected phenol derivatives of formula III may be made, for example, by using an analogous procedure to process (a) above, using an aldehyde analogous to formula II but wherein the phenol group has been protected with the group R″. The starting materials of formula V may be obtained, for example, using analogous procedures to those described in European patent application, publication No. 94239.

The necessary Wittig reagents may be obtained, for example, by conventional procedures, for example by treating the corresponding phosphonium halides with a strong base, such as sodium hydride, lithium diisopropylamide, potassium t-butoxide or butyllithium. They are generally formed in situ just prior to carrying out the condensation process (a) above.

The necessary starting materials of formula III may conveniently be, obtained for example, by reacting the corresponding protected acid of formula VI with a sulphonamide of the formula $H_2N.SO_2R^2$ and a suitable dehydrating agent, for example N,N′-dicyclohexylcarbodiimide, optionally together with an organic base, for example 4-(dimethylamino)pyridine, in the presence of a suitable solvent or diluent, for example methylene chloride at a temperature in the range, 10°–50° C., but preferably at or near room temperature. Alternatively, a reactive derivative of the acid of formula VI, for example an acid halide (such as the acid chloride), may be reacted with an alkali metal salt (such as the sodium salt) of the appropriate sulphonamide, conveniently at or near room temperature and in a suitable solvent or diluent, for example an ether, N,N-dimethylformamide or methylene chloride.

When a salt of a compound of formula I is required, it may be obtained by reaction with the appropriate base affording a physiologically acceptable cation, or by any other conventional procedure.

Further, when an optionally active form of a compound of formula I is required, one of the aforesaid processes is carried out using an optically active starting material. Alternatively, the racemic form of a compound of formula I may be reacted with an optically active form of a suitable organic base, for example ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure for example using an aqueous mineral acid such as dilute hydrochloric acid.

Many of the intermediates defined herein are novel, for example the phenol derivatives of formula III, and are provided as further separate features of the invention.

As stated earlier, the compounds of formula I are antagonists of one or more of the actions of TXA$_2$, for example certain of its actions on blood platelets, the vasculature and/or the lung. The antagonism may be demonstrated in one or other of the following standard tests:

(a) The rabbit aortal strip model devised by Piper and Vane (*Nature*, 1969, 223, 29–35) or the rat aortal strip model developed by Kennedy et alia (*Prostaglandins*, 1982, 24, 667–689) using as agonist the TXA$_2$ mimetic agent known as U46619 (described by R L Jones et alia in "Chemistry, Biochemistry and Pharmacological Activity of Prostanoids" edited by S M Roberts and F Scheinmann, at page 211; Pergamon Press, 1979) may be used as the agonist; and (b) a blood platelet aggregation test based on that described by Born (*Nature*, 1962, 194, 927–929) and involving:

(i) aggregating human, citrated, platelet-rich plasma by addition of the TXA$_2$ mimetic agent U46619 so that a dose-response curve is generated;

(ii) generating a dose-response curve for U46619 stimulated platelet aggregation in the presence of increasing amounts of test compound (generally in the range $10^{-5}$M to $10^{-10}$M); and (iii) calculating a $K_B$ value indicating potency of TXA$_2$ antagonism for the test compound, averaged over several concentrations, from the calculated 50% response value for U46619 aggregation in the presence and absence of test compound; and (c) a bronchoconstriction test involving measuring the inhibition by a test compound of the bronchoconstriction induced in the Konzett-Rossler, anaesthetised guinea-pig model (as modified by Collier and James, *Brit.J.Pharmacol.*, 1967, 30, 283–307) by intravenous administration of the TXA$_2$ mimetic agent, U46619 and involving:

(i) obtaining a cumulative dose-response curve to U46619 induced bronchoconstriction by intravenous administration of constant volumes of increasing concentrations of U46619 (0.2–4 μg/kg) in physiological saline solution and expressing bronchoconstriction as the maximum of that theoretically obtainable with no air flow to the test animal;

(ii) generating a cumulative dose-response curve to U46619 induced bronchoconstriction at 30 minute intervals for 3 hours after oral dosing of test compound; and (iii) calculating a dose-ratio for the test compound (that is the ratio of concentration of U46619 required to cause 50% bronchoconstriction in the presence and absence of test compound) indicating the potency of TXA$_2$ antagonism.

The antagonism of the effects of TXA$_2$ on the vasculature may be demonstrated, for example in rats in the following manner:

(d) Male rats (Alderley Park strain) are anaesthetised with sodium pentobarbital and blood pressure is monitored at the carotid artery. The TXA$_2$ mimetic agent U46619 is administered intravenously at 5 μg/kg via the jugular vein to produce 20–30 mm/Hg (2640–3970 pascal) increase in systolic blood pressure. The process is repeated twice to ensure adequacy of response. A test compound is then administered either intravenously (via the jugular vein) or orally (via a cannula) directly into the stomach and the animal challenged with U46619, five minutes after dosing with test compound and then successively every ten minutes until the hypertensive effect of U46619 is no longer blocked.

Further, the antagonism of the effects of TXA$_2$ in vivo may be demonstrated, for example, by assessing the effects of a test compound on the aggregation of blood platelets obtained after administration of test compound to a test animal, such as a rabbit, rat, guinea pig or dog, using standard procedures similar to that described in (a) above. However, when the aggregation of dog platelets is being studied it is necessary to use a predetermined, threshold concentration of the platelet aggregation agent adenosine diphosphate (about 0.4–1.2×$10^{-6}$M) together with the TXA$_2$ mimetic agent, U46619.

By way of illustration, the compound described in the accompanying Example 1 hereafter possesses a $K_B$ of 5.4×$10^{-9}$M in procedure (b) above.

In general, other compounds of formula I show the following levels of TXA$_2$ antagonist properties in one or more of the above mentioned tests e.g. test (a) $pA_2>6.0$; test (b) $K_B$: $<1.0\times10^{-6}$M; test (c) dose ratio$>5$, 2 hours after oral dosing at 10 mg/kg or less and/or test (d), significant inhibition of U46619 induced hypertension for at least 1 hour following oral dosing at 25 mg/kg or less, without any overt toxicity in tests (c) or (d).

As stated previously, the compounds of formula I may be used in the therapy or prevention of diseases or adverse conditions in warm-blooded animals in which it is desirable to antagonise one or more of the actions of TXA$_2$. In general, a compound of formula I will be administered for this purpose by an oral, rectal, intravenous, subcutaneous, intramuscular or inhalation route, so that a dose in the range, for example 0.01–5 mg/kg body weight, will be given up to four times per day, varying with the route of administration, the severity of the condition and the size and age of the patient under treatment.

The compounds of formula I will generally be used in the form of a pharmaceutical composition comprising a compound of formula I, or a pharmaceutically acceptable salt thereof, as defined hereinabove, together with a pharmaceutically acceptable diluent or carrier. Such a composition is provided as a further feature of the invention and may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; and in the form of a powder, together with pharmaceutically acceptable inert solid diluents such as lactose, for administration by insufflation.

The pharmaceutical compositions may be obtain by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The pharmaceutical compositions of the invention may also contain one or more agents known to be of value in diseases or conditions intended to be treated; for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition. A composition according to the invention may also advantageously contain an inhibitor of thromboxane $A_2$ synthetase, for example dazoxiben or furegrelate (U.63557).

In addition to their use in therapeutic medicine, the compounds of formula I are also useful as pharmacological tools in the development and standardisation of test systems for the evaluation of the effects of $TXA_2$ in laboratory animals such as cats, dogs, rabbits, monkeys, rats and mice, as part of the search for new therapeutic agents. The compounds of formula I may also be used because of their $TXA_2$ antagonist properties in helping to maintain the viability of blood and blood vessels in warm-blooded animals (or parts thereof) under-going artificial extracorporeal circulation, for example during limb or organ transplants. When used for this purpose a compound of the formula I, or a physiologically acceptable salt thereof, will generally be administered so that a steady state concentration in the range, for example, 0.1 to 10 mg. per liter is achieved in the blood.

The invention will now be illustrated in the following non-limiting Examples in which, unless otherwise stated:

(i) evaporations were carried out by rotary evaporation in vacuo;

(ii) operations were carried out at room temperature, that is in the range 18°–26° C. and under an atmosphere of an inert gas such as argon;

(iii) flash column and medium pressure liquid chromatography (MPLC) chromatography were performed on Merck Kieselgel (Art. 9385) obtained from E. Merck, Darmstadt, W. Germany;

(iv) yields are given for illustration only and are not necessarily the maximum attainable;

(v) proton NMR spectra were normally determined at 90 or 200 MHz in $CDCl_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet;

(vi) all end-products were isolated as racemates.

EXAMPLE 1

Ethanethiol (0.75 ml) was added over 15 minutes to a stirred suspension of sodium hydride (485 mg, 50% w/w dispersion in oil) in 1,3-dimethyl-3,4,5,6-tetrahydro-2(1H)-pyrimidinone (DMPU) (25 ml) at 4° C., maintained under an argon atmosphere. After 10 minutes the temperature was raised to 80° C. and a solution of N-methanesulphonyl-4(Z)-6-([2,4,5-cis]-2-[1-methyl-1-phenoxyethyl]-4-o-methoxyphenyl-1,3-dioxan-5-yl)hexenamide (A) (871 mg) in DMPU (5 ml) was added. The mixture was stirred for 3.5 hours at 80° C. and for a further 1 hour at 100° C., then cooled to 10° C. and poured into an ice-water mixture (100 ml). The aqueous mixture was washed with dichloromethane (2×50 ml). The aqueous phase was acidified to pH3 with 2M hydrochloric acid and extracted with ether (3×50 ml). These extracts were washed with water (2×50 ml) and saturated brine (50 ml), then dried ($MgSO_4$) and evaporated. The oil obtained was purified by flash chromatography, using hexane/ethyl acetate/acetic acid (60:40:1 v/v) as eluant, to give N-methanesulphonyl-4(Z)-6-([2,4,5-cis]-2-[1-methyl-1-phenoxyethyl]-4-o-hydroxyphenyl-1,3-dioxan-5-yl)hexenamide as a colourless oil (456 mg); NMR: 1.37 (6H, s), 1.88 (2H, m), 2.33 (4H, m), 2.67 (1H, m), 3.22 (3H, s), 4.00 (1H, dm J=11 Hz), 4.22 (1H, dd J=11,1 Hz), 4.78 (1H, s), 5.32 (1H, d J=2 Hz), 5.40 (2H, m), 7.08 (9H, m); m/e 521 $(M+NH_4)^+$.

The starting material (A) was obtained as follows:

(i) A solution of (4-o-methoxyphenyl-2,2-dimethyl-1,3-dioxan-cis-5-yl)acetaldehyde, (European patent application, publication No. 94239A, p41) (15.8 g) in dry THF (75 ml) was added under argon to a stirred, ice-cooled solution of the ylid prepared from (3-carboxypropyl)triphenylphosphonium bromide (51.48 g) and potassium t-butoxide (26.88 g) in dry THF (400 ml). The mixture was stirred for 15 minutes at 4° C., then for 1.5 hours at ambient temperature and was then poured into ice-water (1 liter). The mixture obtained was washed with 50% v/v ether/hexane (2×250 ml) to remove the bulk of neutral material. The aqueous phase was acidified to pH 5 with acetic acid and extracted with ether (4×300 ml). These extracts were washed successively with water (3×150 ml), and saturated brine (2×100 ml), then dried ($MgSO_4$) and evaporated. The residue was purified by flash chromatography, eluting with toluene/ethyl acetate/acetic acid (80:20:2 v/v). The solid obtained was crystallised from 10% v/v ethyl acetate/hexane (250 ml) to give 4(Z)-6-(4-o-methoxyphenyl-2,2-dimethyl-1,3-dioxan-cis-5-yl)hexenoic acid (B) (13.0 g), m.p. 99°–101° C.; NMR: 1.52 (3H, s), 1.54 (1H, m), 1.56 (3H, s), 1.80 (1H, m), 2.28 (4H, m), 2.49 (1H, m), 3.77 (1H, dd J=11,1 Hz), 3.82 (3H, s), 4.16 (1H, dm J=11 Hz), 5.28 (2H, m), 5.45 (1H, d J=2 Hz), 6.82 (1H, dd J=7, 1 Hz), 6.97 (1H, td J=7, 1 Hz), 7.22 (1H, td J=8, 1 Hz), 7.48 (1H, dm J=8 Hz).

(ii) A suspension of the hexenoic acid (B) (1.5 g) in 2-methyl-2-phenoxypropionaldehyde (3.0 g) containing p-toluenesulphonic acid (10 mg) was stirred for 18 hours at ambient temperature and then heated at 60° C. for 6 hours. The cooled solution was diluted with ether (30 ml) and extracted with 0.5M sodium hydroxide solution (3×10 ml). The aqueous extracts were washed with ether (20 ml), then acidified to pH5 with acetic acid and extracted with ether (3×15 ml). These extracts were washed successively with water (2×10 ml) and saturated brine (10 ml), then dried ($MgSO_4$) and evaporated. The residue was purified by MPLC, eluting with hexane/ethyl acetate/acetic acid (85:15:1 v/v), to give 4(Z)-6-([2,4,5-cis]-2[1-methyl-1-phenoxyethyl]-4-o-methoxyphenyl-1,3-dioxan-5-yl)hexenoic acid (C) as a clear oil (655 mg); NMR: 1.34 (3H, s) 1.42 (3H, s), 1.57 (1H, m), 1.89 (1H, m), 2.30 (4H, m), 2.49 (1H, m), 3.81 (3H, s), 3.98 (1H, dm J=11 Hz), 4.15 (1H, dd J=11, 1 Hz), 4.80 (1H, s), 5.24 (1H, d J=2 Hz), 5.32 (1H, m), 6.85 (1H, ddJ=7, 1 Hz), 7.03 (4H, m), 7.24 (3H, m), 7.43 (1H, dd J=7, 1.5 Hz); m/e 458 $(M^++NH_4)$, 441 $(M^++H)$.

[The necessary 2-methyl-2-phenoxypropionaldehyde was itself obtained as follows:

A stirred solution of methyl 2-methyl-2-phenoxypropionate (3.88 g) in dichloromethane (100 ml) was treated dropwise at −70° C. under argon, with a 1M solution of diisobutylaluminium hydride (dibal) in dichloromethane (21 ml). The solution was stirred for 1 hour at −70° C., then allowed to warm to −30° C., after which it was poured into a vigorously stirred aqueous solution of potassium sodium tartrate tetrahydrate (50 g) dissolved in water (100 ml) cooled to 4° C. After stirring for 30 minutes, the mixture was separated by filtration through diatomaceous earth. The filtrate was extracted with ether (4×100 ml) and the extracts were washed with saturated brine (2×100 ml), dried (MgSO$_4$) and evaporated. The residual oil (3.18 g) containing 2-methyl-2-phenoxypropionaldehyde was used without further purification.]

(iii) Dicyclohexylcarbodiimide (1.08 g) was added to a solution of the oil C (2.13 g), 4-(dimethylamino)pyridine (0.61 g) and methanesulphonamide (0.48 g) in dichloromethane (20 ml). The mixture was stirred for 1 hour at 4° C. then for 18 hours at ambient temperature. The precipitated N,N'-dicyclohexylurea was removed by filtration by filtration, and washed with dichloromethane. The filtrate and washings were extracted with 0.1M sodium hydroxide (65 ml). The basic extract was acidified with acetic acid and extracted with ether (3×50 ml). These extracts were washed with water (2×50 ml) and saturated brine (50 ml), then dried (MgSO$_4$) and evaporated. The oil obtained was purified by MPLC, eluting with hexane/ethyl acetate/acetic acid (75:25:1 v/v), to give N-methanesulphonyl-4(Z)-6-([2,4,5-cis]-2-[1-methyl-1-phenoxyethyl]-4-o-methoxyphenyl-1,3-dioxan-5-yl)hexenamide (A) as a clear oil (1.77 g); NMR: 1.35 (3H, s), 1.42 (3H, s), 1.52 (1H, m), 1.94 (1H, m), 2.36 (4H, m), 2.54 (1H, m), 3.21 (3H, s), 3.83 (3H, s), 4.00 (1H, dm J=11 Hz), 4.18 1H, dd J=11, 1 Hz), 4.79 (1H, s), 5.27 (1H, d J=2 Hz), 5.37 (2H, m), 6.88 (1H, bd J=7 Hz), 6.99 (1H, td J=7, 1 Hz), 7.09 (3H, m), 7.27 (3H, m), 7.42 (1H, m); m/e 535 (M+NH$_4$)+.

EXAMPLE 2

An illustrative dosage form of a composition of the invention is provided by the following capsule formulation:

|  | mg/capsule |
| --- | --- |
| Compound X * | 10 |
| Lactose Ph. Eur | 588.5 |
| Magnesium stearate | 1.5 |

The capsules may conveniently be of hard gelatine and are filled in conventional manner. Compound X* is a compound of formula I or a salt thereof as defined hereinbefore, for example the compound of Example 1 or a salt thereof.

Chemical Structures referred to herein

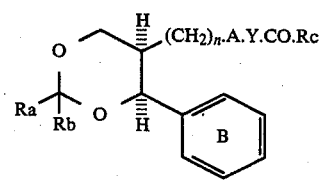

-continued
Chemical Structures referred to herein

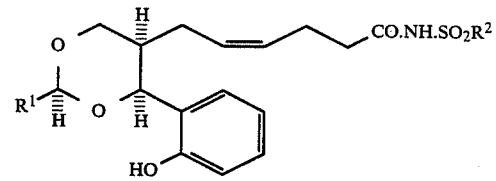

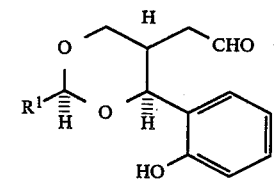

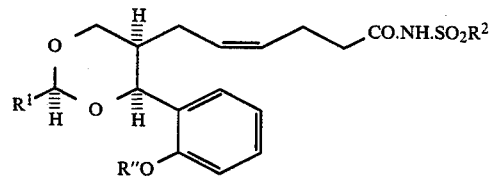

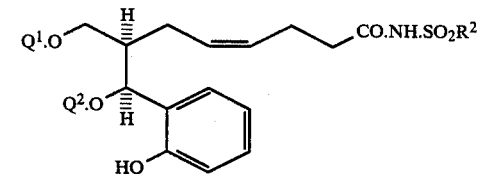

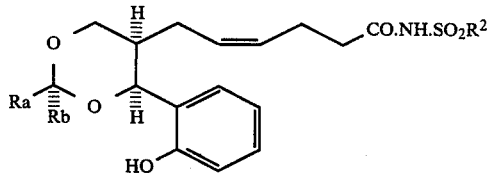

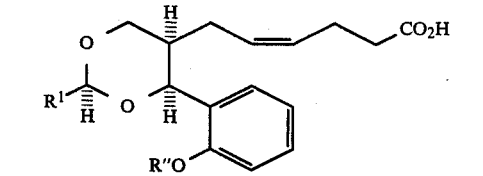

What is claimed is:
1. A sulphonamide derivative of the formula I set out below

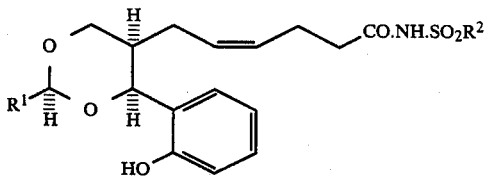

wherein R$^1$ is a group of the formula R$^3$O.CR$^4$R$^5$— in which R$^3$ is (1–6C)alkyl or phenyl, the latter optionally bearing a substituent selected from halogeno, cyano, nitro, trifluoromethyl and (1–4C)alkoxy, and R$^4$ and R$^5$ are independently (1–4C)alkyl; and R$^2$ is (1–6C)alkyl, benzyl or phenyl, the latter two of which may optionally bear a halogeno, (1–4C)alkyl, (1–4C)alkoxy, trifluoromethyl, cyano or nitro substituent; and the substituents at positions 4 and 5 of the dioxane ring in formula I and the substituent $R^1$ have cis-relative stereochemistry; or a pharmaceutically acceptable salt thereof.

2. A compound as claimed in claim 1 wherein $R^3$ is methyl, ethyl, propyl, isopropyl or phenyl, the latter optionally bearing a substituent selected from fluoro, chloro, bromo, cyano, nitro, trifluoromethyl, methoxy and ethoxy; $R^4$ and $R^5$ are independently methyl or ethyl; and $R^2$ is methyl, ethyl, propyl, benzyl or phenyl, the latter two optionally bearing a fluoro, chloro, bromo, methyl, ethyl, methoxy, ethoxy, trifluoromethyl, cyano or nitro substituent.

3. A compound as claimed in claim 1 wherein $R^1$ is 1-[(1-4C)alkoxy]-1-methylethyl or 1-methyl-1-phenoxyethyl, the latter optionally bearing a fluoro, chloro, bromo, cyano or nitro substituent on the phenoxy moiety, and $R^2$ is methyl, ethyl or phenyl, the latter optionally bearing a fluoro, chloro, bromo, cyano, nitro, trifluoromethyl or methoxy substituent.

4. A compound as claimed in claim 1 wherein $R^1$ is 1-methoxy-1-methylethyl or 1-methyl-1-phenoxyethyl.

5. A compound as claimed in claim 4 wherein $R^2$ is methyl or ethyl.

6. N-Methanesulphonyl-4(Z)-6-([2,4,5-cis]-2-[1-methyl-1-phenoxyethyl]-4-o-hydroxyphenyl-1,3-dioxan-5-yl)hexenamide, or a pharmaceutically acceptable salt thereof.

7. A salt as claimed in any one of claims 1-6 which is selected from alkali metal, alkaline earth metal, aluminium and ammonium salts, and from salts with organic amines and quaternary bases forming physiologically acceptable cations.

8. A pharmaceutical composition for antagonizing one or more of the actions of thromboxane $A_2$ which comprises a thromboxane $A_2$ antagonistically effective amount of a compound of formula I, or a pharmaceutically acceptable salt thereof, as claimed in claim 1, together with a pharmaceutically acceptable diluent or carrier.

9. A composition as claimed in claim 8 which comprises as an additional active ingredient, an inhibitor of thromboxane $A_2$ synthesis.

10. A method of antagonising one or more of the actions of thromboxane $A_2$ in a warm-blooded animal requiring such treatment which comprises administering to said animal an effective amount of a compound of formula I, or a pharmaceutically acceptable salt thereof, as claimed in claim 1.

11. N-Methanesulphonyl-4(Z)-6-([2,4,5-cis]-2-[1-methyl-1-phenoxyethyl]-4-o-methoxyphenyl-1,3-dioxan-5-yl)hexenamide, or a salt thereof.

* * * * *